United States Patent [19]

Mason, Jr. et al.

[11] Patent Number: 5,143,551
[45] Date of Patent: Sep. 1, 1992

[54] SINGLE USE INKING CARD FOR FINGERPRINTING

[75] Inventors: Stanley I. Mason, Jr.; David S. Draeger, both of Weston, Conn.

[73] Assignee: Crisis Communication, Inc., Weston, Conn.

[21] Appl. No.: 461,295

[22] Filed: Jan. 5, 1990

[51] Int. Cl.⁵ .............................................. A61B 5/117
[52] U.S. Cl. ................................... 118/31.5; 118/269; 118/500; 427/1
[58] Field of Search ................. 118/31.5, 264, 269, 118/500; 427/1

[56] References Cited

U.S. PATENT DOCUMENTS

| | | | |
|---|---|---|---|
| 1,833,287 | 11/1931 | Hadley | 118/31.5 |
| 2,500,612 | 3/1950 | Krogh | 118/31.5 |
| 2,938,292 | 5/1960 | Jaskowsky et al. | 427/1 |
| 3,467,055 | 9/1969 | Yonchar | 118/31.5 |
| 3,664,910 | 5/1972 | Hollie | 118/31.5 |
| 3,720,304 | 3/1973 | Laugherty et al. | 118/31.5 |
| 3,839,960 | 10/1974 | Bissonet | 118/31.5 |
| 3,867,164 | 2/1975 | Orlando et al. | 118/31.5 |
| 4,182,261 | 1/1980 | Smith, III et al. | 118/31.5 |
| 4,363,286 | 12/1982 | Leavitt et al. | 118/31.5 |
| 4,699,077 | 10/1987 | Meadows et al. | 118/31.5 |
| 4,706,600 | 11/1987 | Mason, Jr. et al. | 118/31.5 |

FOREIGN PATENT DOCUMENTS

86/01392  3/1986  PCT Int'l Appl. .................. 427/1

Primary Examiner—Jay H. Woo
Assistant Examiner—Khanh P. Nguyen
Attorney, Agent, or Firm—Haynes N. Johnson

[57] ABSTRACT

A single use fingerprint inking card for use in making fingerprints including a front sheet and a back sheet, the sheets being secured together in overlapping relationship, the front sheet being cut to define a plurality of openings with hinged reclosable panels covering the openings, an inking sheet having fingerprint ink on one side and secured between the front sheet and the back sheet with the side bearing the ink facing the openings, so that the panels can be individually opened to expose the fingerprint ink and thereafter closed to cover it. The nature of the inking sheet and the ink are such that the ink tends to cling to the inking sheet, not the facing sheet.

5 Claims, 1 Drawing Sheet

U.S. Patent    Sep. 1, 1992    5,143,551
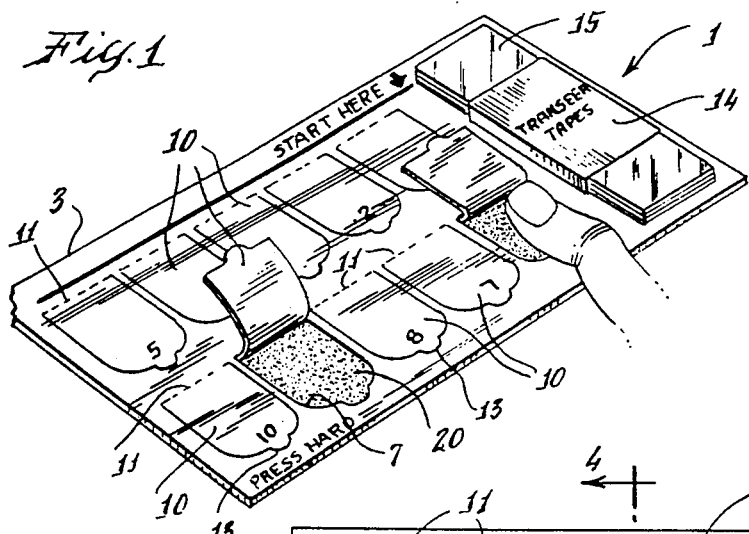
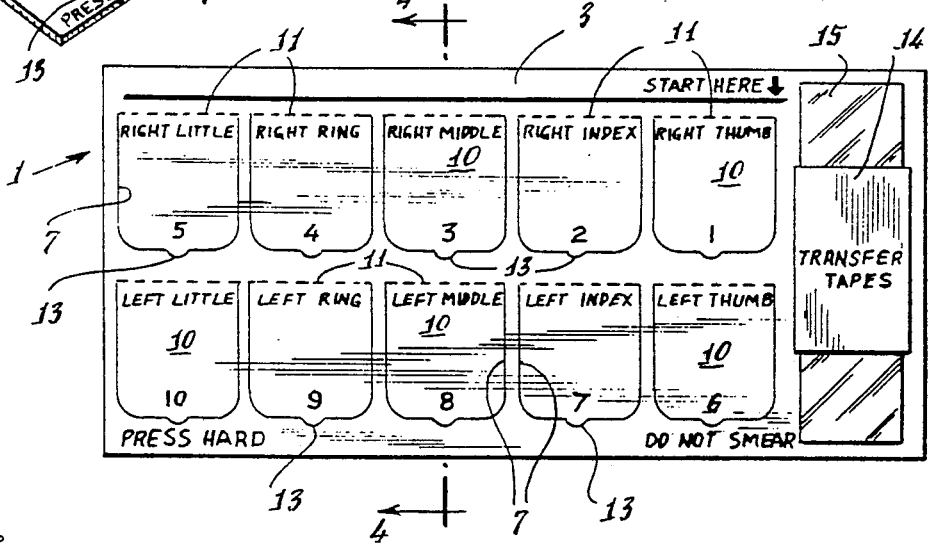
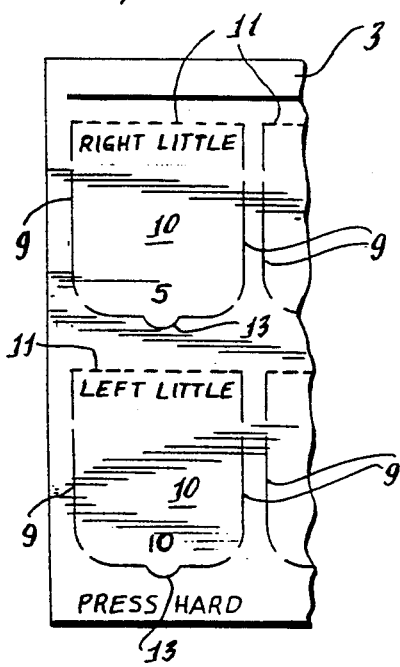
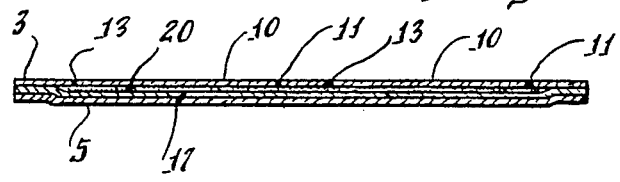
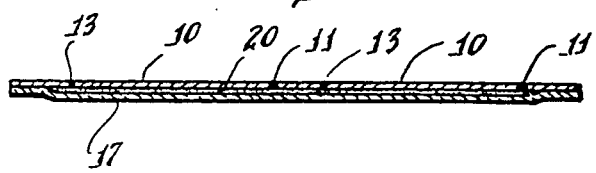

SINGLE USE INKING CARD FOR FINGERPRINTING

FIELD OF THE INVENTION

This invention relates to the field of fingerprinting and, in particular, to a card used to carry and dispense ink.

BACKGROUND OF THE INVENTION

One of the inventors herein was a co-inventor in U.S. Pat. No. 4,706,600 on "Kit For Making Sets Of Transparent Fingerprints Using Differential Adhesion," the disclosure of which is incorporated herein by reference. In that patent dry ink was used for fingerprinting and was applied to the fingers with a dauber. The present invention is believed to be an improvement over that system.

BRIEF SUMMARY OF THE INVENTION

In the present invention we substitute what we call an inking card for the dauber. This card has front and back sheets with an intermediate thin sheet carrying a coating of black fingerprint ink printed on the upper surface of the inner sheet. The front sheet has ten scored areas, one for each finger, which can hinge open to reveal the ink underneath. These hinged panels can be opened one at a time, a finger pressed against the ink, and then closed again. The thickness of the ink is preferably just enough for one print, so that the proper quantity of ink goes on the finger, just enough to make a good print and not so much as to result in a smudged print. When this thickness is used, the card is a single use card.

DESCRIPTION OF THE DRAWINGS

FIG. 1 is a perspective view of our inking card. Two of the panels are shown open, one so the black fingerprint ink can be seen and the other so that one can see how a finger is pressed against the ink.

FIG. 2 is a plan view of the inking card, showing how the panels can be numbered to show a sequence of use, and labelled to suggest which finger should be used for each opening. This labelling provides the advantage of preventing the user from using the same ink area for more than one finger.

FIG. 3 is a partial plan view showing how the front of the card can be scored or clicked out to form a reclosable, hinged panel covering the opening.

FIG. 4 is a section taken on line 4—4 of FIG. 2 showing the front and back sheets of the card and the inking sheet in between them.

FIG. 5 is similar to FIG. 4, showing a modification in which the backing sheet has been omitted.

DETAILED DESCRIPTION OF THE INVENTION

Our inking card 1 includes a front sheet 3 and a rear sheet 5. These sheets can be two sheets adhered together along their edges with an adhesive or can be a single folded sheet. The front sheet has been scored or clicked to define a plurality of openings 7 each closed with a hinged panel 10, with hinges 11, and a tab 13 on the opposite end of the panel from the hinge to aid in opening the panel and then in keeping the panel closed, once that area has been used.

The scoring 9 is not complete enough to allow the panels to open, but is complete enough to permit the user to break them free simply by bending the inking card in the area of the tab 13. The tab 13 will then project outwardly and can be grasped to open the panel.

The front sheet 3 and rear sheet 5 are preferably made of a thin card which can flex sufficiently to allow the scoring 9 on the front sheet 3 to be broken. We prefer using a card with a smooth, glossy finish. This serves to reduce the possibility of the ink adhering to the inner surface of sheet 3. A card or sheet made of 20 to 60-lb offset works satisfactorily.

If desired, a space can be provided on the front sheet 3 for a sleeve 14 carrying transfer tapes 15 of the type described in the above-mentioned patent.

Preferably, the ink itself is dry fingerprint powder 20 carried by inking sheet 17. Alternatively, it may be a semi-moist ink, if desired. Sheet 17 may be of tissue and has a roughened surface, such as found in facial tissue, better to hold the ink. Sheet 17 is secured between front sheet 3 and back sheet 5 with the side facing the openings 7 in front sheet 3. Sheet 17 is adhered along its edges to the inner surface of either sheet 3 or sheet 5 or both.

Our fingerprint powder 20 is a dry ink somewhat like black rouge or eye shadow. One formulation, in descending order of importance, is made of carbon (about 75 to 90%), zinc stearate (10 to 15%), isopropyl palmitate (5 to 10%), and lanolin oil (2 to 5%), with concentrations of less than 1% of methyl parabin, imidazolidinyl urea, propylparaben, and BHA. The powder is initially carried in a vehicle, such as water or alcohol and can be applied to the surface of the inking sheet in any desired manner, such as by a rotogravure process. Its thickness should best be less than 1 mil and preferably between about 0.4 and about 0.5 mils, ample enough for one fingerprint, but not so much as to cause the print to smudge.

It is best if the surface of inking sheet 17 has a greater adherence for the powder than the inside surface of front sheet 3. This is accomplished by having sheet 17 with a somewhat rough surface, as with tissue, and the inside surface of sheet 3 (panels 10) being smooth or coated, i.e., the surface of the inking sheet is rougher than that of the inside surface of sheet 3. In this way the powder will cling to the inking sheet and not to panel 10. This is useful in that it maintains the powder on sheet 17 at a uniform thickness and avoids having it exposed on the back of an opened panel 10, with risk of it unintentionally getting on the user's hands or clothing.

The front sheet 3 or panels 10 may be printed with indicia to identify specific fingers 22 and sequence of use 24.

To reduce costs, the modification of FIG. 5 can be used. The structure is the same as before, except that the back sheet 5 has been omitted.

When one desires to make fingerprints, he flexes card 1 near the tab 13 for the intended finger, causing the tab to project outwardly so that it can be grasped and used to open the particular panel 10. This exposes the ink so that the finger can be pressed against it and become coated. If the ink is of the proper thickness, the finger will pick up about 70% to 90% of the ink where the fingerprint ridges touch the paper. The inked finger is then pressed against whatever medium is to record the print, such as the transfer tapes 15 disclosed in the previously-mentioned patent. Because of the thickness of the ink, most of it will be transferred from the finger to the medium, leaving the finger relatively clean. Panel 10 can then be closed, with tab 13 catching the edge of opening 7 and so holding panel 10 closed. In a similar manner the remaining panels can be opened and the ink used.

If desired, the ink may be packaged for individual fingerprints, one finger only. This could be done by having the ink on an inking sheet with a single front sheet as a covering. Alternatively, the ink could be carried on pads dimensioned slightly greater than the size of the finger, with the top surface carrying a dry ink, and the back surface acting as a cover sheet for the inked sheet beneath it. Here, the ink should have greater adherence for the top of the sheet than for the back.

We claim:

1. A single use, reclosable fingerprinting inking kit usable to apply dry ink to fingers so that fingerprints can be placed elsewhere, said kit including a front sheet and a back sheet secured together in overlapping relationship, said sheets being formed of flexible card, said front sheet being cut to define at least one opening therein, with a hinged panel covering said opening, said opening being surrounded on all sides by other portions of said front sheet, said cut being of such strength that said panels will open when said sheets are flexed, means for securing said panel shut after it has once been opened, an inking sheet having fingerprint powder on one side thereof, said powder having a thickness between about 0.4 and about 0.5 mil, and said inking sheet being secured between said front sheet and said back sheet with the side bearing said powder facing said openings, whereby said panel can be individually opened to expose said fingerprint powder, a finger can then be pressed against said powder to receive the proper amount of ink to make a full, but unsmudged print, and the kit can thereafter be interlocked closed to cover the remaining said powder.

2. A kit as set forth in claim 1 in which said inking sheet has greater adherence for said fingerprint powder than does the side of said panel facing said inking sheet.

3. A kit as set forth in claim 1 in which the side of said inking sheet bearing said fingerprint powder has a rougher surface than does the side of said panel facing said inking sheet.

4. A kit as set forth in claim 1 in which said means for securing said panel shut is a tab on said panel at the end opposite said hinge.

5. A kit as set forth in claim 1 in which there are a plurality of openings in said front sheet.

* * * * *